United States Patent [19]

Herweck et al.

[11] Patent Number: 5,722,964
[45] Date of Patent: Mar. 3, 1998

[54] FILTERED BLOOD COLLECTION DEVICE

[75] Inventors: Steve A. Herweck, Nashua; Theodore Karwoski, Hollis; Nicholas Want, Manchester, all of N.H.

[73] Assignee: Atrium Medical Corporation, Hudson, N.H.

[21] Appl. No.: 487,468

[22] Filed: Jun. 7, 1995

Related U.S. Application Data

[63] Continuation-in-part of Ser. No. 404,108, Mar. 13, 1995, abandoned.

[51] Int. Cl.⁶ ..................................................... A61M 1/00
[52] U.S. Cl. ........................... 604/317; 604/4; 604/321
[58] Field of Search ................................... 604/317, 318, 604/319, 320, 321, 324, 406

[56] References Cited

U.S. PATENT DOCUMENTS

| | | | |
|---|---|---|---|
| 3,646,935 | 3/1972 | Holbrook | 604/319 |
| 3,805,788 | 4/1974 | Kleiner | 604/320 |
| 4,744,785 | 5/1988 | Rosenthal | 604/319 |
| 4,798,578 | 1/1989 | Ranford | 604/4 |
| 4,870,975 | 10/1989 | Cronk | 604/317 |
| 4,892,529 | 1/1990 | Valerio | 604/317 |
| 4,911,697 | 3/1990 | Kerwin | 604/318 |
| 4,988,342 | 1/1991 | Herweck et al. | 604/321 |
| 5,087,250 | 2/1992 | Lichte | 604/319 |
| 5,286,262 | 2/1994 | Herweck | 604/317 |
| 5,318,510 | 6/1994 | Cathcart | 604/317 |

OTHER PUBLICATIONS

"Pleur–Evac: Cardiotomy Reservoir Autotransfusion System" brochure, 1994.
"Pleur–Evac Plus A–9350" photograph of product, 1995.

Primary Examiner—Sam Rimell
Assistant Examiner—Luke Yeh
Attorney, Agent, or Firm—Lahive & Cockfield, LLP

[57] ABSTRACT

A blood collection vessel includes a blood inlet, a pooling region in which blood from the inlet collects, and an outlet in the pooling region for reinfusion of the collected blood. A filter located in the blood path between inlet and outlet extends at least in part into the pooling region and impounds clots so they remain away from the outlet but suspended in the collected blood. Preferably, the filter is located to provide venting between both sides of the filter. In one embodiment the filter is a vertical wall, which defines a shielded outlet column or chimney extending above the outlet. Blood permeates to the outlet region over a broad area, and the column forms an open suction path that prevents suction differentials from arising across the filter, so clots cannot be sucked through the large-pore material. With the clots residing in the collected fluid, the total fluid loss is directly displayed in a single window at all times, and maximal use is made of the limited volume in the vessel. In another embodiment, the filter constitutes a false floor or basket in the pooling region. A preferred construction employs filter material on a support grid, to form a flexible and self-supporting filter sheet, which inserts like a plate to compartmentalize the collection vessel and form an impounding surface in the pooling region.

17 Claims, 5 Drawing Sheets

FIG. 2B

FILTERED BLOOD COLLECTION DEVICE

REFERENCE TO RELATED APPLICATIONS

This application is a continuation-in-part of Applicant's earlier-filed U.S. patent application U.S. Ser. No. 08/404, 108 filed on Mar. 13, 1995, abandoned, the priority of which is hereby claimed. That application and the earlier patents on which it relies, including Applicant's earlier U.S. patents identified below, are all incorporated herein by reference.

BACKGROUND

The present invention relates to blood collection or autoinfusion devices such as are used for postoperative and intraoperative blood collection to collect bleeding and fluid loss from a patient. These devices have evolved over the last several decades from two basic lines of medical instruments. The first form of device, a cardiotomy reservoir, is a bottle or bucket assembly operating much like a vacuum cleaner, and used to collect loose blood during cardiac surgery. These devices are generally large unobstructed covered vessels which connect to a vacuum supply and have a suction wand to suck up loose pools of blood within the operating arena. The second form of device, generally referred to as a chest drain, is a relatively compact bedside vessel used to collect fluids postoperatively from a closed surgical site, e.g., from a drain tube implanted in the patient's chest. These latter devices generally operate with a much smaller magnitude of suction, in the range of negative 15 to 22 centimeters of water and typically include either a dry or wet suction regulator mechanism, as well as a water seal or one-way valve which prevents direct entry of atmospheric air into the blood collection chamber of the drain device. Since these devices apply their suction to the chest cavity and may be acted on by, or may affect motion of the lungs within the chest cavity, they generally also contain various forms of release valves to prevent excessive levels of either pressure or suction from occurring in the patent drain line.

Over the last several years, each of these devices have come to include some form of blood filter which allows the collected fluid to be cleared of clots and debris so that it may be safely reinfused back into the patient. This practice obviates or reduces the need for external units of blood in cases when there is a large bleed, or a continuing relatively clean bleed such that the collected blood remains suitable for prompt re-use. The general design concepts for blood reinfusion were pioneered with massive blood loss using cardiotomy reservoirs employed for open heart bypass surgery, and the concept of postoperatively reinfusing collected blood following chest trauma or open thoracic surgery has evolved from this first form of cardiopulmonary collection devices and has therefore retained similar internal elements. For example, the commercially available postoperative and intraoperative blood collection devices generally collect and screen blood clots as the blood enters the collection chamber. The common design approach for these devices has been to collect and isolate the large clots and keep them separated from a pool of the patient's infusible blood. Chest drains, formerly used simply to collect blood and dispose of it, now employ the same filter concept of collecting and isolating clots as the blood enters. In the case of chest drains, where the thoracotomy tube is attached to a closed wound in the patient's chest, and the level of suction is of relatively small magnitude, it is quite important to keep the tube or entrance of the device from becoming obstructed by clot material. This is accomplished in some current chest drain designs by employing a large filter, housing, or a flowover design to prevent clots from backing up and occluding the inlet port. However, to accommodate massive bleeding, either the filter itself must have a large area or the filter chamber must be relatively large to accommodate the slowdown in flow and backing up which occurs as blood permeates through the filter, especially when clot material contacts and smears over the filter.

Simultaneous with the trend toward collection for reinfusion and the concomitant need for filtration of blood, there has been a progression or improvement of pharmacological techniques over the last several years, in addition to improved intraoperative blood management techniques, and changes in blood management immediately following surgery, which all affect the quantity and size of clots that now enter modern day autotransfusion collection devices. Not only have these factors changed the nature and course of postoperative bleeding since the post-operative reinfusion collection devices were introduced almost a decade ago, but, the vast number of operative procedures now being performed result in an increased number of situations at the extremes of a normal distribution, where large mounts of clot material are passed. Even devices which were designed with overflow protection and large open filter pathways for the blood inlet, may sometimes fill up with larger size clots beyond the capacity of the filter or filter chamber, and may potentially place the patient at risk due to occlusion of the blood inlet or due to clots passing over or through the filter and obstructing the blood outlet.

For example, if a filter chamber is not entirely closed and is capable of overflowing at its top or side, then a massive bleeding episode may cause stringy clots to overflow or be carded with a flow of blood into a main collection chamber below. When this occurs, the overflow of clots may increase the potential to block the exit port or reinfusion line at some point during the autotransfusion procedure. Such an occurrence, while infrequent, may be life threatening if it prevents a significant amount of reinfusible blood from being evacuated from the collection system during autotransfusion. These incidents of blockage are commonly referred to in the industry as "clot down". Simply stated, clot down is the occurrence of an unexpected occlusion in the reinfusion circuit due to clotting in the collection chamber, or migration of rather large clots through the exit port of the chamber. It should be noted, that reinfusion devices of this sort do not generally filter the blood on the way out of the chamber, but instead have only a fine filter located in the IV set to the patient. This fine filter in the IV line is easily blocked if it encounters a clot.

Some collection devices address this problem by providing little or no avenue for large clots to overflow, instead requiring all blood from the inlet to pass through a relatively large mesh sock filter hanging from the inlet en route to the outlet. Such collection devices initially used relatively small filter socks, which had a high potential for closing off or smearing over with clots, and for occluding the inlet. Later, relatively large filter sock assemblies were used, presenting a much greater surface area, so that at least some portion of the surface would remain open for blood to overflow out of the sock through a clean portion of the filter wall. However, even a large filter sock causes fluid to pool or impound above the smeared over area and has the potential, in the event of a massive bleed, of becoming sufficiently clogged that it entirely fills up and occludes the inlet opening. Furthermore, once a sock is entirely smeared over, differences in suction may arise between the inside and outside of the sock, causing clots to be sucked through. To avoid drawing clots through the filter, some overflow or bypass is required to maintain an open suction path, equalizing pressure on both sides of the filter. This can require special loops of tubing extending above the drain device, or equalizing vent conduits within different portions of the collection vessel.

Another problem encountered in filtering blood is that larger clots tend to hold up more liquid or fluid drainage in the gross filter. Since collection devices typically display the volume of collected fluid which has accumulated in a pooling region of filtered blood at the bottom of the device, the retention of a fraction of the fluid drainage in the filter assembly masks the true extent of the patient's actual blood loss, and prevents the attending medical personnel from accurately assessing the total volume of blood loss. Medical attendants must regulate the patient's fluid replacement by accurately reading all drainage and fluid output, so the skewed reading introduced by separation of clots and associated drainage may affect treatment. Furthermore, if larger clots cause more fluid to hold up in the filter, small bleeding trends become harder to detect or anticipate by looking only at the display of collected filtered blood, which generally changes more slowly and with a lag. This can prevent or at least delay appropriate diagnosis or intervention.

Thus, the problem of properly filtering collected blood for reinfusion and avoiding untoward events during patient recovery presents three primary concerns. These are:

1. the stockpiling of significant amounts and larger clots during drainage collection from the patient which can potentially block the primary inlet and prevent fluid evacuation from the patient's chest;

2. clot down of the transfusion circuit, which may occur unpredictably when clots overflow or pass by a gross blood filter and subsequently are drawn into the exit port to block the line and stop the reinfusion of blood back to the patient; and 3. holding back of blood, which impairs evaluation of blood loss.

Accordingly, improvements in autotransfusion blood collection devices are desirable.

BRIEF DESCRIPTION OF THE INVENTION

The present invention solves the foregoing problems by providing a blood collection vessel with an inlet for collecting blood from a patient, a pooling region wherein the collected blood resides in the collection chamber, and an outlet located at the pooling region for reinfusing the collected blood back into the patient. A filter barrier is located in a fluid path between the inlet and the outlet and extends into the pooling region to impound clots so that they cannot reach the outlet, yet they reside in suspension in the pooling region as fluid is being collected. In a preferred embodiment, the filter barrier is a vertically oriented filter wall. An overhanging eave below the inlet deflects entering clots and blood above the top of the wall, and channels incoming blood away from the side of the wall. The other side of the wall bounds an outlet column or air space over the outlet port, into which the nonclotted collected fluid seeps without suctional draw through the filter, so blood may be quickly evacuated without damage to red blood cells. In another embodiment, the filter barrier may be a false floor formed of filter material secured to a support lattice, and extending over the floor above the level of the outlet. In this case, the filter is preferably inclined so that clot material gravitates to an end or side of the filter, while remaining suspended in a fluid bed, and the other end or side of the filter remains open, i.e., not covered by clots.

In the preferred embodiment, the vertical orientation of the filter wall together with the overhung deflector deflects the flow of incoming blood and prevents clotty drainage from smearing over the face of the filter as it enters the collection chamber. This assures that a major portion of the filter wall remains open to allow suction equalization throughout the chamber. In particular, when fluid is withdrawn through the outlet which could result in increased suctional loading on the outlet side of the filter, this suctional loading communicates, through the air column above the outlet, with the open top of the filter, so no suction differential can arise across the filter. Thus, the suction distribution in the chamber does not vary or cause clotted material to be sucked through the filter. This construction avoids collected blood cells being physically traumatized by being actively drawn through the filter. The pooling of clot material in the collection pool allows the clots to reside in liquid suspension where they remain fluidized rather than being isolated and becoming desiccated. The clots also form part of the full volume of blood loss, visible in the collection monitoring window, providing a direct reading of total fluid loss and permitting a more knowledgeable management of the patient's fluid balances. Furthermore, by allowing the clots to actually enter the collection chamber, rather than requiring a separate isolation chamber with buffer capacity, the limited volume available in the collection vessel for blood collection is fully utilized, so that the collection vessel is implemented in a smaller space than a prior art vessel of like capacity.

In a preferred construction the filter consists of an open mesh 220 micrometer filter fabric attached to a semiflexible support grid, which in turn is held in place by friction against a plurality of molded support braces or insert slots in the body of the collection chamber. This filter assembly may for example be a semirigid sheet which simply inserts into a slot in the chamber, and locks in position to form a divided compartment by placing the front face panel over the body. At the top of the vertical filter of the preferred embodiment, a sloped or angled deflector rib is placed directly under the inlet hole about an inch or more away to divert clotty drainage away from, and to one side of the filter therebelow. The deflector rib is overhung so that the clotty drainage falls straight at the bottom of the rib to the floor of the collection chamber without contacting the filter wall. The front face includes a clear window aligned next to the filter, on the side opposite the clot collection side, to show the graduated level of blood collection on the outlet side vertical column. By deflecting the inlet path to the other side of the filter, smearing over the front face plate by oncoming blood is also avoided, and a clearly defined fluid fill line is presented in the visible outlet column. Furthermore, the outlet column fills without splashing or fluctuation, by gentle permeation through the filter at or below the level of collected fluid. Fluid graduations at this position therefore provide a highly stable and accurate indication of fluid loss. Both the deflector rib, and the vertical filter wall may terminate at a support protrusion located somewhat behind the front face to assure that flowing incoming fluid does not run along the front face or otherwise obscure visibility therethrough.

BRIEF DESCRIPTION OF THE DRAWINGS

These and other features of the invention will be understood from the description below taken together with the drawings, wherein.

DETAILED DESCRIPTION

Figure 1:
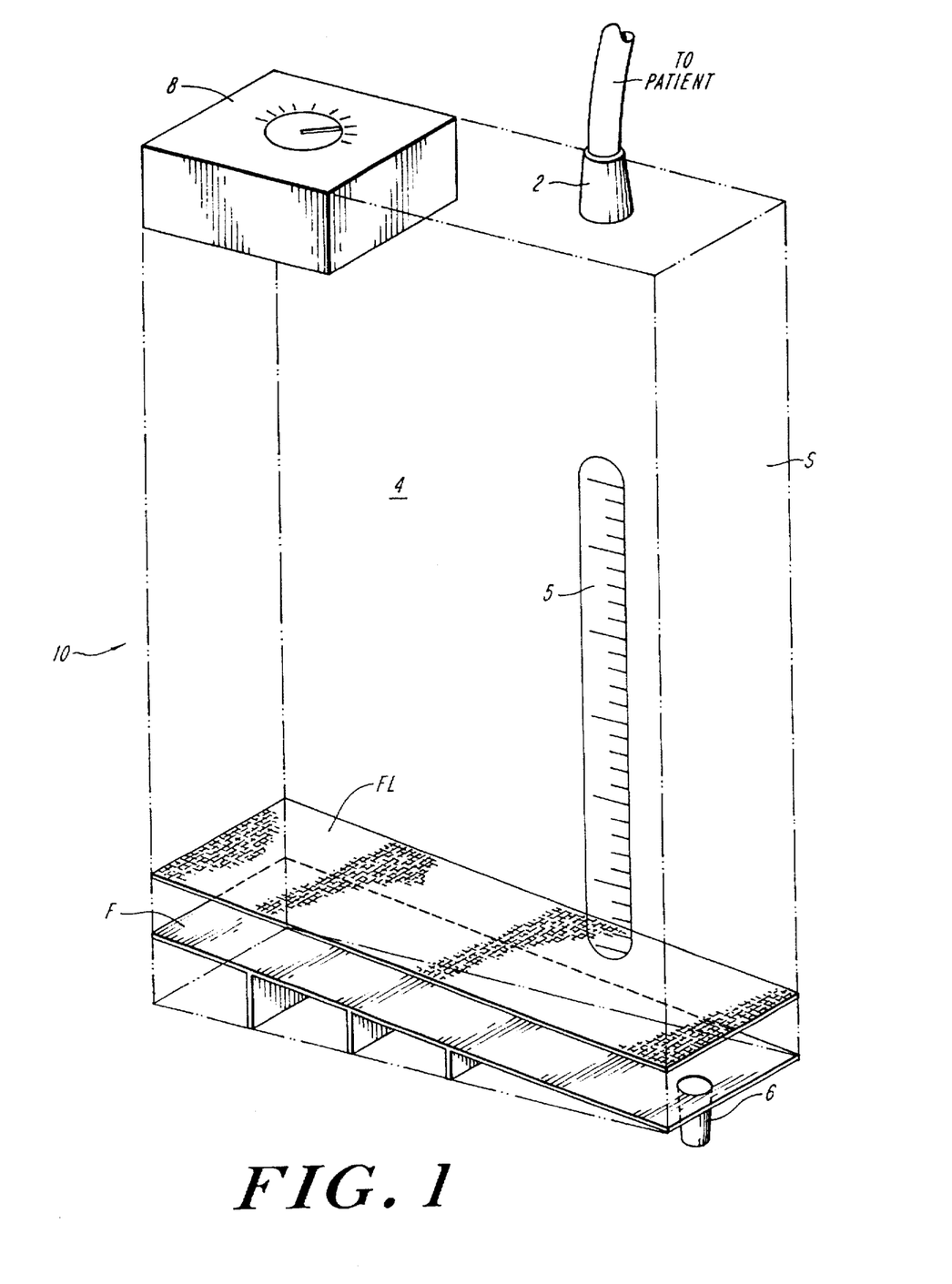
FIG. 1 shows a front perspective view of a blood collection device in accordance with the present invention.

FIG. 1 shows one embodiment of a blood collection drain vessel 10 in accordance with the present invention. Drain vessel 10 comprises a generally box-like container 4 having a suction setting assembly 8 at one side thereof, and an entrance port 2 for a patient drain tube located away from the suction setting assembly 8. As shown schematically in the Figure, a set of volume graduations 5 are disposed across a face of the container to indicate the volume of collected fluid residing in the bottom of the container, and an outlet 6 is provided for reinfusing collected blood. The foregoing elements are indicated schematically, and a great degree of variation exists in the implementation of the suction control portion and in the position and layout of the fluid collection chamber. The suction control mechanism may consist of an entirely "dry" type of regulator which operates as a bleeder or air dilution valve to modulate the suction from a hospital wall suction fitting so that the chamber experiences an underpressure between approximately 20 and 30 centimeters H₂O. Alternatively, the suction regulator may include a so-called "wet" regulator assembly which has a column of water with a nominal height equal to the desired suction level. This is generally achieved by having one or more arrangements of U-shaped tubes or columns formed within the housing, as shown in Applicant's earlier U.S. Pat. Nos. 4,988,342; 5,286,262; 5,397,299 and others. In either case, a seal chamber or check valve arrangement is generally provided between the suction setting portion and the collection chamber itself to prevent back passage of air into the collection chamber. This is necessary because the collection chamber, being connected by a drain tube to the patient's chest cavity, is itself subject to bursts of positive or negative pressure due to patient spasms, breathing and the like. In general the suction regulation assembly occupies a substantial amount of space within the container 4, and the seal chamber or valve makes a further incursion into the interior volume of the vessel, so that the actual amount of space available for collected blood or filtered fluid within the chamber is less than the full volume of the box 4. By way of example, in the devices illustrated in Applicant's aforesaid patents, which have a liquid manometer chamber, this chamber is typically 3 to 5 centimeters wide and extends for the full height of the box, while the seal chamber may be partially tucked under portions of the suction setting chamber, but still requires a tall vertical chimney encroaching another centimeter or so laterally into the volume of the container. With a filter located in an upper region of the collection chamber, approximately 1800–2200 cc volume can be realized for collected fluid below. In these devices, the geometry of the water columns makes overall shape of the box taller than it is wide. In the case of the drainage vessels having a dry suction control assembly, the various valve or regulator mechanisms for such assembly are typically located along the top of the device or on one side of the chamber near the top of the device. These can occupy less vertical space than a wet suction regulator, although there is a tendency to utilize suction control mechanisms which have antechambers or buffer chambers to smooth the response of the opening and closing valve involved in the regulator assembly, and these may also occupy a significant volume of the available space within the chamber. In any case, in various embodiments of the present invention suction regulation assembly 8 may be of either the wet or dry type.

Continuing now with the description of FIG. 1, the suction established within the vessel 10 by the regulator assembly 8 draws fluid from the patient's wound site or from a vacuum wand (generally at a higher suction setting) through inlet 2 and into the collection chamber, where it pools at the bottom region. As shown, the drain device 10 has a floor denoted F which is inclined at a slight angle toward the outlet 6 so that blood entering the assembly pools in the bottom and drains downhill to the outlet. In the illustrated embodiment, a plurality of plastic ribs 11 support the floor, and the box itself is one unitary molded housing, closed by a clear plastic face plate (not separately drawn) as described in Applicant's aforesaid U.S. patents.

In accordance with a principal aspect of the present invention, a filter denoted FL is provided immediately adjacent to the floor F and in this embodiment extending over substantially the full area of the floor F above the outlet 6. The gap between the filter and the floor defines a narrow interstitial drainage space of filtered fluid, and clots are retained above the filter while the filtered fluids may flow freely along the floor down to the outlet. In the illustrated embodiment, the filter FL is formed of a 220 micron mesh filter material which is supported on a thin plastic grid work so that the filter assembly as a whole forms a semirigid but flexible sheet. Protruding plastic hubs or ridges may be formed in the body to support or align the grid so that the sheet fits securely and is not prone to dislodgment. While a flat filter is shown, the filter may be bowed slightly from side to side to provide a larger filter area and also create an enlarged flow space between the filter and the floor in the central region, or may be formed in another shape entirely, for example, as a deep basket supported by ribs and nested at the floor of the drain vessel. Whichever form the filter takes, the filter impounds blood clots on the inlet side of the filter, while being located in the pooling region so that the impounded clots reside in fluid suspension in the surrounding collected fluid. With this arrangement, there is no separate filter chamber, but rather a filter barrier in the pooling region of the collection chamber, which prevents clots from reaching the outlet but does not physically isolate them from the collected blood. As shown, the area of the filter is relatively large, at least several square inches and for dimensions of a typical collection chamber at least ten to fifteen square inches. Thus, even though the filter may be entirely covered by clot material as it resides in collected fluid, there is a large area of filter which allows unclothed blood to seep through at a relatively high rate as fluid is being withdrawn from outlet 6.

The filter material is sized to catch larger particulate material and macroemboli, so that blood which seeps through the mesh and reaches the outlet is suitable for reinfusion. In general the infusion line will have a finer microembolus filter in-line, to remove finer pyrolytic or embolism-forming material.

Figure 1A:
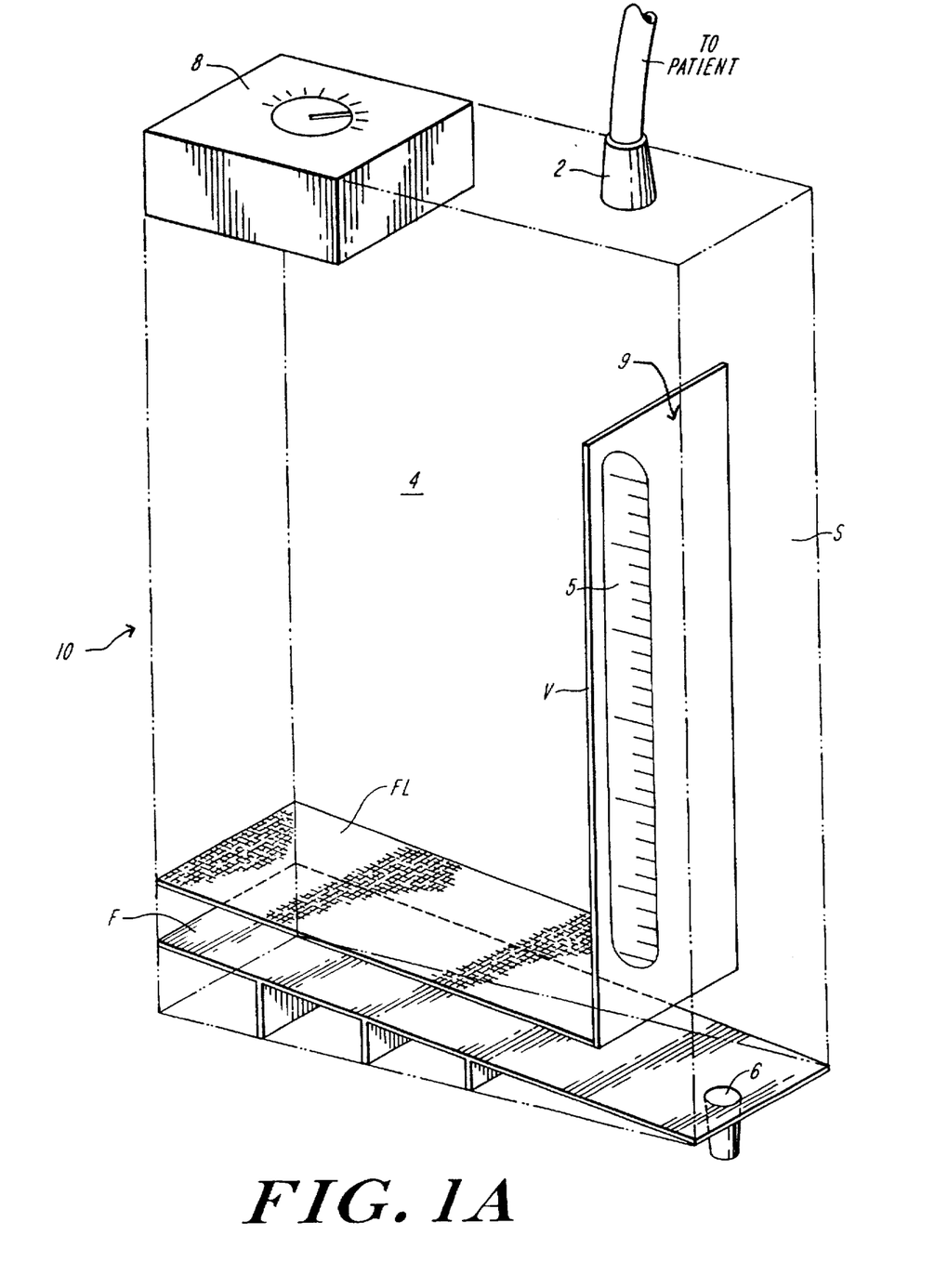
FIG. 1A shows a variation of the embodiment of FIG. 1.

FIG. 1A shows another embodiment of the invention similar in some ways to the filter collection structure shown in FIG. 1. In this embodiment, rather than extending over the full area of the floor, the filter, FL extends to a vertical separator wall, V, which is spaced a small distance from the sidewall, S, of the vessel. This creates a chimney or vent space 9 directly over the outlet 6. As illustrated, the vent space 9 is defined by the narrow gap between the wall V and the chamber wall S and it extends vertically upward over the outlet 6 to the top of the vertical wall V. As a result, pressure in the space 9 experienced by the outlet is the same as pressure existing at any point in the collection chamber on either side of the vertical wall V. The chimney 9 communicates directly with the space between the filter FL and the floor F, as well as with the space in the chamber above the vertical wall V, so the suction level below the filter is no greater than the suction level on the fluid lying above. Blood is therefore driven through the filter solely by the hydrostatic pressure of fluid accumulated thereover. This prevents clots from being sucked through the filter or around the edges of the filter. In other embodiments, the filter may form a concave trough or bucket that catches all clots, but does not extend entirely to the front (or back) wall. Such construction leaves a vent space around the edges of the filter to assure that the outlet does not introduce pressure differentials that would suck clots through the filter.

Figure 2:
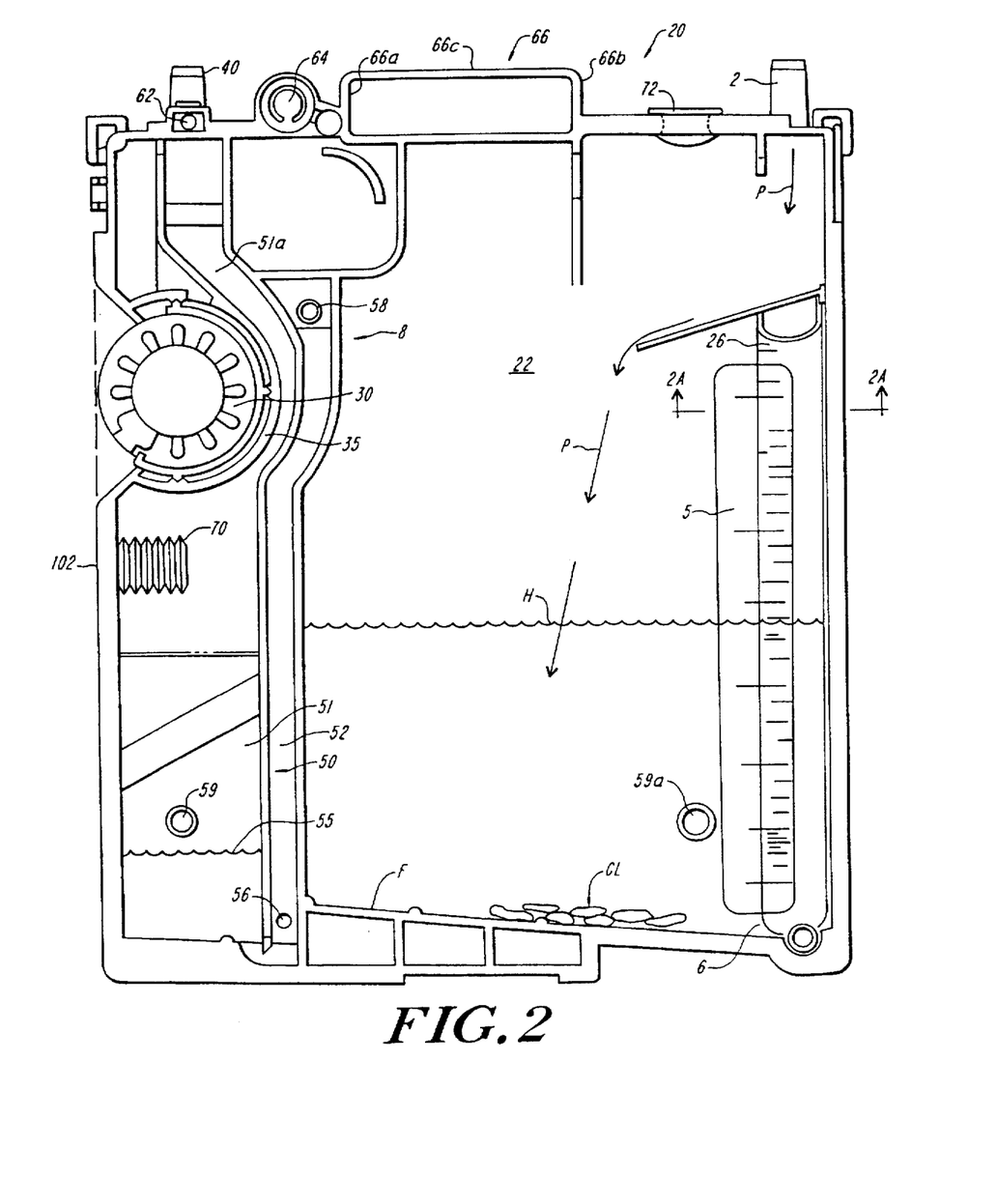
FIG. 2 shows another embodiment of the invention.

In another embodiment of the invention shown in FIG. 2, the filter is oriented differently to serve both as a barrier to corral the clots in fluid suspension, and as a porous separating wall that maintains uniform suction distribution throughout the chamber. In this embodiment, the vessel 20 has a suction control section indicated generally by 8 on the left side of the vessel while the right side, indicated generally by 22, consists entirely of a large unobstructed collection volume. As in the preceding embodiment, the patient fluid inlet 2 is located at an upper corner or side, and fluid enters via a drain tube whence it travels along a path P to the lower collection region of the chamber 22. The outlet 6, although not illustrated, resides in the same location as the previous embodiment, and an eave or deflector plate 24 is mounted in the housing below the patient inlet 2 and directly above the outlet 6. Eave 24 deflects incoming fluid, diverting it a few centimeters to the side and forming a spillway for entering blood so that it falls down into the collection chamber without smearing the graduation window 5, which as before, is located near the right hand edge of the box. The eave 24 may be angled or curved in order to more effectively channel blood away from the face plate as well as channel it laterally to one side. Below the eave 24, a vertical wall 26 formed of a filter material extends from the floor upwardly to a point just below the eave, with the whole wall 26 being entirely sheltered under the eave so that blood and clots entering along the inlet flow/drip path P will neither enter it from above nor contact its face.

In the preferred embodiment illustrated in FIG. 2, the vertical wall 26 is formed of a sheet of filter material and porous supporting material, bent around into a U-shaped column so that it stands above the region of the outlet 6. It thus forms an open breathing tube or chimney above the outlet, which in use fills with filtered blood that permeates in to the center through the surrounding or circumferential filter wall. The stiffness of the filter 26 is such that the bent sheet is self-supporting, and is fixedly secured within the housing by contact pressure when the face plate is assembled over it. The dimensions of the filter, by way of example, for a two-inch deep vessel approximately eleven inches tall, are approximately five inches wide by nine inches tall. Thus, when the 5-inch wide rectangle is bent into a U-shape, it fits snugly within the compartment formed by the housing and the front face. By bending the filter in a U-shape, a large surface area e.g. 45 square inches is obtained. Alternatively, a two-inch wide strip extending from the floor to the eave 24, and from the back wall to the front face, could be used. In that case, however, the rate of fluid permeation through the wall could be lower, and it would further be necessary to provide slots, nubs or positioning elements in the vessel body to align and secure the filter.

Figure 2A:
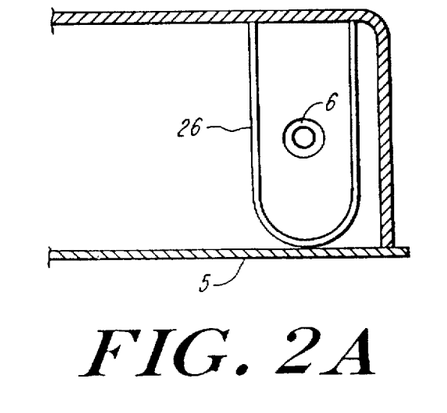
FIG. 2A illustrates a sectional detail of the embodiment of FIG. 2.

FIG. 2A illustrates a horizontal section of the filter region in the illustrated position of the embodiment of FIG. 2.

Operation of the device is as follows:

When a suction source is connected at the left hand side of the vessel, the suction regulator mechanism establishes a continuing suctional draw of approximately 20 centimeters of water in the chamber 22. Blood and fluid are drawn from the patient via the patient tube, and travel by gravity into the vessel following the path P. Deflector plate 24 deflects the inlet path laterally to one side, so that blood and clot material pass to the bottom of the vessel. As fluid builds up, clots are retained on the left side, or outside, of the filter, while fluid permeates through the filter and achieves a similar level inside the filter and above the outlet 6. As noted above, the filter has a large surface area, e.g., approximately 45 square inches, and at any give time, when a certain amount of fluid has entered, the clot material denoted CL collects at the bottom and resides suspended in the fluid. When the clots and fluid attains a height H (in inches), this surrounds an end portion of the filter having an area 5H (in$^2$) through which the fluid seeps. Above the outlet, the volume enclosed within the curved filter 26 remains free of clots and thus assures that the outlet maybe drawn down without causing clot-down or misfunction of the outlet line. Furthermore, the portion of filter 26 residing above the level H is not touched by incoming fluid, and remains entirely porous and permeable to air so that the suction levels within and without the filter chimney are identical, and differential pressure forces do not arise which might otherwise suck clots through the filter, or subject blood cells to excessive mechanical trauma or desiccation from flow of air.

While the filter 26 has been illustrated as large area curved filter sheet, the filter barrier wall 26 may be implemented as single flat sheet, comparable to filter FL of FIG. 1, but oriented vertically. In that case, various struts or slots in the face plate, the vessel body, or both are provided to align and hold the filter wall without allowing seepage past its edges.

In each of the foregoing embodiments, the graduation window 5 is placed at the right hand edge of the vessel, above the lowest point of the floor, so that it reads fluid collection starting with very low levels of collected volume, e.g., approximately 5 to 10 milliliters. In each case the volume graduations display the total amount of fluid collected, whether in the form of blood or fluidized clots, and thus there is no need for the technician to visually assess the amount of clot material held in a separate region or pooling chamber such as is done with vessels of the prior art. In addition, because all of the fluid gravitates immediately to the floor of the vessel, rather than being withheld at some upper seep-through chamber, the center of gravity of the vessel is very low and the collection vessel of the present invention enjoys exceptional stability against tipping or knocking over. In addition, because this is no separate filter chamber and thus no need to provide a pooling region which is offset from the floor of the vessel as well as having an upper clearance of several inches from the inlet to prevent blockage, the entire assembly is implemented in a box which is smaller than a conventional chest drain assembly of the same collection volume. Applicant has found, for example, that a collection volume equivalent to a prior art drain may be obtained in vessel approximately 20 percent smaller than prior art vessels. The smaller size and enhanced stability result in ease of handling and reduced risk of mishap.

The embodiment of FIG. 2 is illustrated as a so-called dry drain, in which the suction assembly 8 includes a suction setting valve 30 fitted within a recess that controls the mount air entering the chamber to an amount which reduces to a desired level the amount of suction applied by a wall-fitting suction port 40. A water seal column 50 operates in a conventional manner as a one-way valve between the suction regulator and the fluid collection chamber 22. Water seal 50 includes a first or large column 51 and a second or narrow column 52 in which a pooling region 55 of approximately several centimeters of water act as a one way check valve for flow of air out of the collection chamber. In this embodiment, a float ball 56 rides up and down in the column 52 to indicate the level of excess suction prevailing in chamber 22. Briefly when suction in chamber 22 exceeds the level of suction applied by the suction regulator 30, the water level in column 52 rises and the position of the float ball 56 thus warns an attendant of dangerous conditions of excessive negativity. At the top of column 52, a check ball 58 impedes the further rising of water so that the pool of water 55 is not depleted and water leaking past the check ball harmlessly collects above the ball and returns to the column when suction again reaches normal levels. Preferably, the leaky check ball 58 is configured to self-release after a short time interval, as described in Applicant's above referenced earlier U.S. Pat. No. 5,114,416.

The water seal chamber 50 maybe filled directly through the suction inlet 40 which as illustrated is located directly above column 51. The upper region of column 51 curves around as shown at 51A about the portion of the housing which receives the suction regulator mechanism. While only a centimeter or two is required in the pooling region 55 to form an effective seal, the indicator ball 56 employs a column 7 to 8 inches high to meter the exact level of excess negativity in the chamber, up to 20 centimeters, and this constraint results in the vessel having a more or less conventional size and shape, but with a height of only about 10 inches to accommodate the illustrated column. However, in other embodiments, the water seal and float valve may be replaced by an entirely dry flap valve or similar assembly making the suction regulation unit more compact, as illustrated for example in FIG. 1. In yet other embodiments, rather than a dry suction regulator, a 20 centimeter water column may be set up to provide regulation of suction to a fixed level, set by the height of the water column, as illustrated in each of applicant's aforesaid U.S. patents.

Among other features appearing in the drawing and not specifically mentioned above are also a positive pressure relief valve 62, which is a simple check valve at the top of the large water seal arm 51, and an excess negativity valve 64 which provides a valved filtered passageway to the atmosphere above the water seal small arm portion 52. Each of these assemblies are described in greater detail in Applicant's aforesaid U.S. Pat. No. 5,397,299. Pierceable septa 59, 59a allow one to conveniently sample or refill the water seal, and to sample collected fluid, respectively. A handle 66 is formed integrally with the body, and like the rest of the body extends to a plane at its front face which is sealed to a transparent face plate that closes the assembly. The handle 66 is thus secured to the body by its vertical edges 66a and 66b, as well as welded to the face plate along both of those edges and along its upper horizontally-oriented face 66c thus forming a rectangular box closed on five of its six sides. This forms an exceptionally secure and strong handle assembly. A removable plug or grommet 72 in the upper surface of the vessel allows one to readily empty residual contents for separate disposal of the device and the biological waste after use. A bellows-type pressure indicator 70 is located in the water seal U-column, above the pooling region of the water seal chamber in column 51, and has its interior communicating with the surrounding atmosphere, so that it expands in length as suction increases in column 51.

Figure 2B:
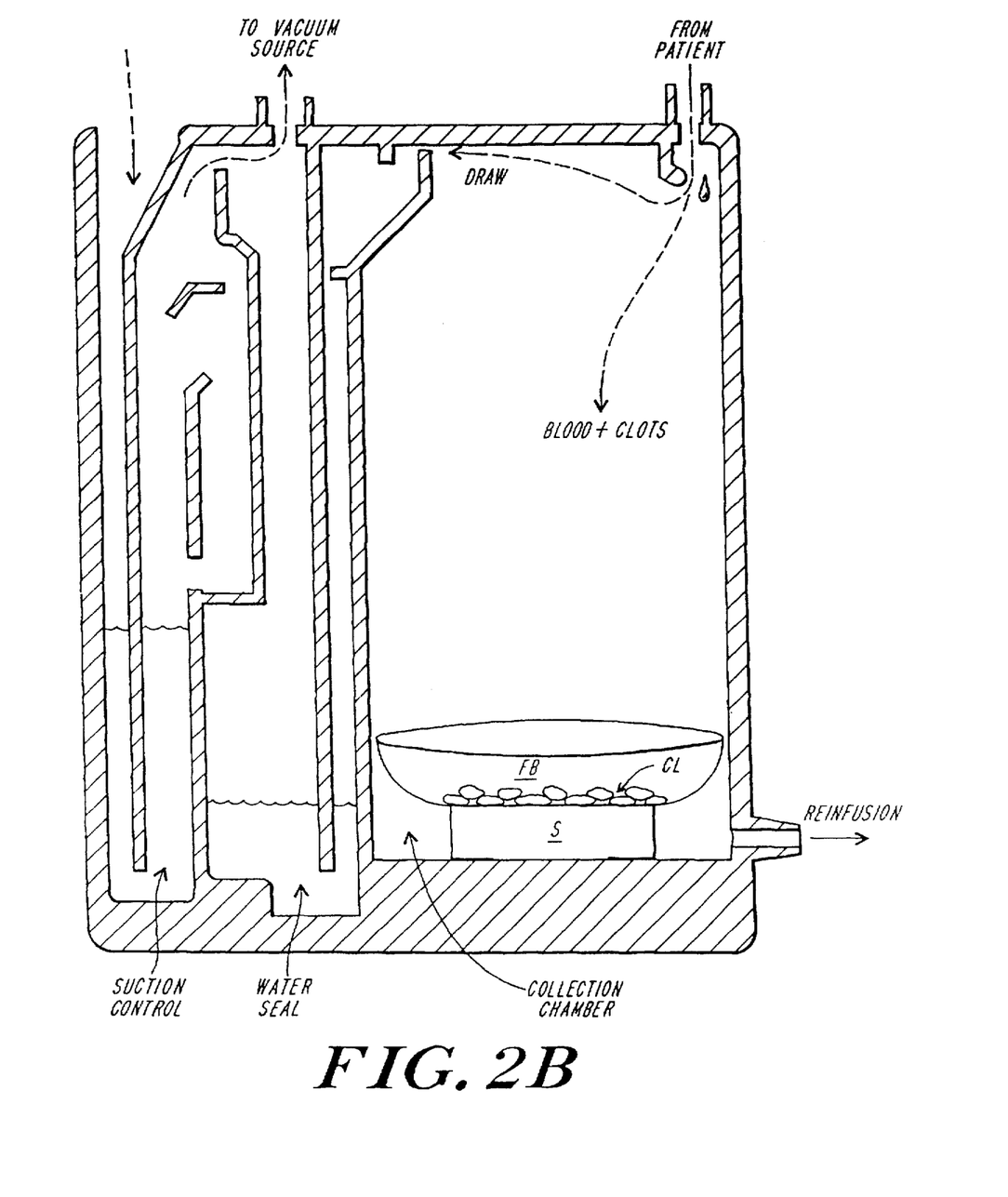
FIG. 2B illustrates another embodiment of the invention.

The collection device of the present invention may also include a filter assembly which takes the general form of a filter basket FB located near the floor of the collection chamber as shown in FIG. 2B. As shown, a pedestal or support S supports a wide-rim filter basket FB shown partly in perspective view which funnels outwardly to catch all incoming fluid, while generally allowing the clots CL to settle and remain harmlessly suspended away from the outlet. The large upper edge area generally assures freedom from blockage so that the fluid outlet does not generate pressure differentials within the collection chamber.

The invention has been described with reference to several particular embodiments; however, it may take other forms which will occur to those skilled in the art, and all such forms are encompassed within the spirit and scope of the present invention, and its equivalent, as defined by the claims appended hereto.

What is claimed is:

1. A wound drainage device for collecting fluid from a patient via a collection tube, such device comprising a collection chamber for collecting the fluid and a suction regulator for regulating suction applied to the collection chamber, wherein the collection chamber includes a top and a bottom and means at an upper region of the device for attaching to the collection tube so that suction in the collection chamber draws in said fluid, an outlet at a lowermost level of the bottom for providing collected fluid to an outlet tube, and a clot catcher extending across the outlet in a barrier position to provide a fluid path to the outlet while allowing clots at the bottom to reside suspended in fluid without reaching the outlet as fluid is withdrawn therefrom.

2. A wound drainage device according to claim 1, wherein the clot catcher includes an open mesh screen.

3. A wound drainage device according to claim 2, wherein the screen is supported by a porous support and forms a flexible and self-supporting barrier wall.

4. A wound drainage device according to claim 3, wherein the porous support is an incline oriented to move collected clots to one side.

5. A wound drainage device according to claim 3, wherein the clot catcher forms a basket.

6. A wound drainage device according to claim 2, wherein the clot catcher forms a chimney above the outlet whereby unfiltered blood surrounds the chimney and permeates through a circumferential area to provide filtered blood to the outlet.

7. A blood collection system for collecting blood and filtering the collected blood for reinfusion or re-use, such system including a vessel with a top and a bottom, an inlet part for connecting to a tube to, draw blood through the tube into the vessel, and with an outlet port at a lower most region of the bottom through which blood collected in the vessel is provided as an output, and a filter within said vessel separating said outlet port from said inlet port, said filter extending to the lowermost region as a barrier across the outlet port to compartmentalize said vessel into a first compartment containing said outlet port and a second compartment away from said outlet port, the first and the second compartments being at a similar level which allows filtered blood to permeate through the filter to the outlet port in the first compartment, while clots impounded in the second compartment remain in suspension in collected blood, wherein said vessel is a rigid vessel and said filter forms a vertical wall separating said first and secured compartments; the two compartments being permeably connected and covered by a common face such that fluid level in either compartment at said face is identical and indicates total volume of fluid which has entered through said inlet.

8. A blood collection system according to claim 7, wherein said filter forms a vertical wall that shields a graduated window from splashing and contact with clots so that level of collected fluid forms a well-defined line that is visible through said window.

9. A blood collection system according to claim 7, further comprising means below said inlet for deflecting incoming blood away from said filter to prevent smearing.

10. A blood collection system according to claim 7, wherein the filter is a self-supporting sheet of open mesh filter having a surface area greater than 50 cm$^2$.

11. A blood collection system according to claim 7, further comprising a graduation window formed on a wall of said vessel for displaying a single volume equal to total blood plus fluid collected.

12. A blood collection system according to claim 11, further comprising means below said inlet for deflecting incoming blood away from said window.

13. A blood collection system according to claim 7, wherein said filter forms a barrier isolating clots from the outlet and from a breather space that equalizes pressure across the filter.

14. A method of collecting blood for reinfusion, such method comprising the steps of
providing a closed collection chamber having a blood inlet at an upper region thereof and a blood outlet at a lowermost region thereof,
applying suction to the collection chamber so that blood is drawn in through the blood inlet, and positioning a filter barrier as a wall extending at least partially in the lowermost region across the outlet to corral blood clots away from the outlet while keeping the clots suspended in fluid collected in said lowermost region, the filter barrier passing filtered blood to the outlet so that blood leaving the outlet is suitable for reinfusion.

15. The method of claim 14, wherein the step of positioning the filter includes positioning the filter to provide a vent passage free of clots that equalizes pressure on both sides of the filter.

16. The method of claim 14, wherein the step of positioning the filter includes positioning the filter to provide a curved wall with enhanced permeation area allowing blood to quickly permeate through the filter as blood is withdrawn through the outlet.

17. The method of claim 14, wherein the step of positioning the filter includes positioning the filter to filter blood channeled by a spillway below the inlet.

* * * * *